(12) United States Patent
Skell (10) Patent No.: US 10,328,361 B2
(45) Date of Patent: Jun. 25, 2019

(54) EXTRACTING SUBSTANCES FROM BOTANICAL MATTER

(71) Applicant: Jeffrey M. Skell, Westborough, MA (US)

(72) Inventor: Jeffrey M. Skell, Westborough, MA (US)

( * ) Notice: Subject to any disclaimer, the term of this patent is extended or adjusted under 35 U.S.C. 154(b) by 549 days.

(21) Appl. No.: 15/053,687

(22) Filed: Feb. 25, 2016

(65) Prior Publication Data

US 2017/0246557 A1 Aug. 31, 2017

(51) Int. Cl.
*A61K 36/00* (2006.01)
*B01D 11/02* (2006.01)

(52) U.S. Cl.
CPC .......... *B01D 11/0219* (2013.01); *A61K 36/00* (2013.01); *B01D 11/0292* (2013.01); *A61K 2236/00* (2013.01)

(58) Field of Classification Search
None
See application file for complete search history.

(56) References Cited

U.S. PATENT DOCUMENTS

| | | | |
|---|---|---|---|
| 6,013,304 A | 1/2000 | Todd | |
| 6,403,126 B1 | 6/2002 | Webster et al. | |
| 7,344,736 B2 | 3/2008 | Whittle et al. | |
| 8,343,553 B2 | 1/2013 | Hospodor | |
| 8,445,034 B1 | 5/2013 | Coles, Jr. | |
| 8,778,418 B2 | 7/2014 | Bisterfeld Von Meer | |
| 8,846,409 B2 | 9/2014 | Flockhart et al. | |
| 8,895,078 B2 | 11/2014 | Mueller | |
| 9,034,395 B2 | 5/2015 | Whittle et al. | |
| 9,044,390 B1 | 6/2015 | Speier | |
| 9,066,910 B2 | 6/2015 | Rosenblatt et al. | |
| 9,169,455 B2 | 10/2015 | Hamler et al. | |
| 9,186,386 B2 | 11/2015 | Speier | |
| 9,199,960 B2 | 12/2015 | Ferri | |
| 2015/0267216 A1 | 9/2015 | Vanhercke et al. | |
| 2016/0270417 A1 | 9/2016 | Corey | |

FOREIGN PATENT DOCUMENTS

EP 0392340 10/1990

OTHER PUBLICATIONS

Dufaure, et al., JACS, 76:1073. (Year: 1999).*
Dufaure, et al., JACS, 76:1081. (Year: 1999).*
Khan, et al., J. Agric. Engng. Res., 28:495. (Year: 1983).*
Kartika, et al., "Twin-Screw Extrusion: A Single Step for Three Treatments of Sunflower Seeds," 16th ISC, Fargo, ND, vol. 2, pp. 805-810. (Year: 2004).*
Kaufmann, et al., Phytochemical Analysis, 13:105. (Year: 2002).*
PCT/US2017/018070, International Search Report dated Apr. 24, 2017, 9 pages.

* cited by examiner

*Primary Examiner* — Michael Barker
(74) *Attorney, Agent, or Firm* — Anderson Gorecki LLP (57) ABSTRACT

A useful substance is extracted from botanical feedstock by mechanically compressing the feedstock and pumping a solvent through the compressed feedstock at high pressure while applying compressive mechanical force against the feedstock. Movement of pressurized solvent through the compressed feedstock may increase the volume of solvent in contact with the feedstock. Flow of solvent under pressure may also present a shearing force that facilitates dissociation of the useful substance from the feedstock.

7 Claims, 7 Drawing Sheets

EXTRACTING SUBSTANCES FROM BOTANICAL MATTER

BACKGROUND

The subject matter of this disclosure relates generally to processing of botanical matter to extract some components found therein while avoiding extraction of other components that may be found therein. A variety of useful therapeutic and non-therapeutic substances are found in different types of botanical matter. For example, willow trees produce salicylic acid which is the active metabolite of aspirin. Other examples include ginseng, goldenseal, digitalis, cascara, wormseed and hemp. Cannabis, which has more recently become recognized for its medicinal properties, contains substances which have therapeutic value for patients with chronic pain, multiple sclerosis, epilepsy and HIV/Aids. Botanical matter may also contain undesirable substances, e.g. natural toxins, heavy metals, or pesticides. Removal of the undesirable substances may increase the value or safety of the botanical matter. Further, extraction of useful substances while avoiding extraction of undesirable substances may help to avoid further processing for purification purposes.

It is known to extract substances from botanical matter using a solvent. For example, dried and milled botanical matter may be mixed with the solvent for some period of time and then physically separated from the botanical matter solids to produce an extracted solution and a residue. Depending upon the intended application for the soluble components and the properties of the solvent, extracts may be used directly, mixed with other components, or the soluble components may be separated from the solvent to produce a concentrate. In order to facilitate separation of the targeted substance from the solvent, the solvent may be selected such that it is a liquid or fluid under the temperature and pressure conditions of the extraction process, and either the solvent or the substance (but not both) is a gas under the temperature and pressure conditions of the separation process. It is also known to effect a liquid phase separation through the addition of a miscible non-solvent or a salt that reduces the solubility of the targeted substance in the solvent. In either case, an efficient extraction is characterized by a rapid and complete dissolution in a small volume of solvent (as concentrated as possible), and a quantitative separation of the extract solution from the residue that may contain plant fibers, waxes, lipids, and liquids that are not dissolved in the solvent. Inefficient extractions take a long time, incompletely dissolve the components of interest (partial extraction), use large solvent volumes (thereby transferring more poorly soluble non-target components), fail to recover all the solvent from the residue, e.g. hand squeezing solvent soaked botanical material through cheese cloth, and transport botanical components via non-solubility mediated mechanism, e.g. plant fragments passing through a course screen or insoluble components (water) ending up in the collection vessel of conventional supercritical $CO_2$ processes.

SUMMARY

All examples and features mentioned below can be combined in any technically possible way. Moreover, potential advantages described herein are not necessarily associated with all implementations, and none of the advantages are required to be realized in order to practice the inventive concepts disclosed herein.

In accordance with an aspect a method comprises: mechanically compressing a botanical feedstock into compressed botanical feedstock; pumping a solvent through the compressed botanical feedstock while applying compressive mechanical force against the compressed botanical feedstock, an amount of at least one substance present in the compressed botanical feedstock dissolving into the solvent to produce partially loaded solvent; and recovering the partially loaded solvent. In some implementations the method comprises reducing moisture content of the botanical feedstock prior to mechanically compressing the botanical feedstock. In some implementations the method comprises reducing average particle size and fiber length of the botanical feedstock prior to mechanically compressing the botanical feedstock. In some implementations the method comprises recirculating the partially loaded solvent by pumping the partially loaded solvent through the compressed botanical feedstock while applying compressive mechanical force against the compressed botanical feedstock to produce partially loaded solvent having a greater concentration of dissolved substance. In some implementations the method comprises pumping unloaded solvent through the compressed botanical feedstock while applying compressive mechanical force against the compressed botanical feedstock after recirculating the partially loaded solvent. In some implementations the method comprises repeatedly recirculating the partially loaded solvent. In some implementations the method comprises applying compressive mechanical force in a range of 0 to 10,000 pound-force per square inch against the compressed botanical feedstock while pumping the solvent through the compressed botanical feedstock. In some implementations the method comprises pumping the solvent through the compressed botanical feedstock at a pressure in a range of 500 to 20,000 pound-force per square inch.

In accordance with an aspect an apparatus comprises: a first solvent reservoir; a second solvent reservoir; a high pressure pump having an inlet port that is connected to the first solvent reservoir; and a hydraulic extraction device that is connected to the high pressure pump and the second solvent reservoir, the hydraulic extraction device applying compressive force against a botanical feedstock while solvent is drawn from the first solvent reservoir by the high pressure pump, pressurized by the high pressure pump, passed through the botanical feedstock in the hydraulic extraction device, and captured in the second solvent reservoir. In some implementations the apparatus further comprises a valve that selectably connects the first solvent reservoir and the second solvent reservoir to the inlet port of the high pressure pump. In some implementations the apparatus further comprises a valve that variably restricts the exit flow from the hydraulic extraction device. In some implementations the hydraulic extraction device applies compressive mechanical force in a range of 0 to 50000 pound-force per square inch against the compressed botanical feedstock while the solvent is pumped through the compressed botanical feedstock. In some implementations the solvent is pressurized by the pump at a pressure in a range of 0 to 100000 pound-force per square inch. In some implementations the hydraulic extraction device comprises a press mounted in a frame. In some implementations the hydraulic extraction device comprises a ram with a channel through which the solvent is introduced to or removed from the botanical feedstock. In some implementations the hydraulic extraction device comprises a base with a channel through which the solvent is introduced to or removed from the botanical feedstock. In some implementations the hydraulic extraction device comprises a porous sintered metal frit.

In accordance with an aspect an apparatus comprises: a base having a cylindrical post section; the base having a channel formed there through via which a fluid can traverse the post; and a cylindrical bore adapted to be temporarily mounted to the cylindrical post section of the base; and a cylindrical ram adapted to move slidably into the cylindrical bore; the ram having a channel formed there through via which a fluid can traverse the ram. In some implementations the filter comprises a porous sintered metal frit. In some implementations the apparatus further comprises a gasket mounted in a groove in the ram. In some implementations the apparatus further comprises a gasket mounted in a groove in the cylindrical section of the base. In some implementations the apparatus further comprises a channel formed through an exterior surface of the base to the filter.

DETAILED DESCRIPTION

Exemplary implementations of the invention will now be described with regard to the attached figures. It should be understood that although certain representative structures, arrangements and materials will be introduced in the description, such structures, arrangements and materials are provided by way of example only, and not as limitations. A wide variety of combinations, replacements or modifications are both possible and within the scope of the inventive concepts. For example, the concepts described herein are not limited to any particular botanical matter or useful substance, or even to the processing of botanical matter. However, botanical matter will be described as the feedstock. The botanical matter used as feedstock may include any of a wide range of different plants and combinations of different plants. Moreover, entire plants or selected parts of plants may be processed.

Figure 1:
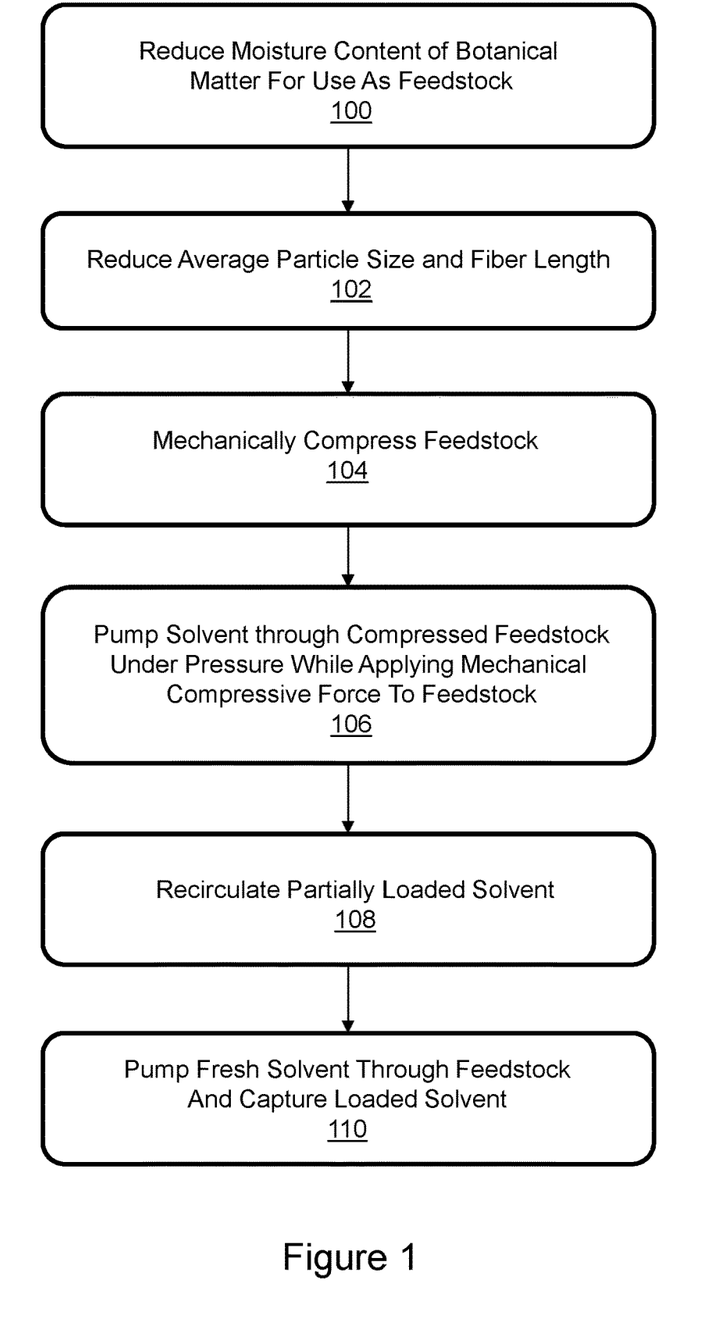
FIG. 1 illustrates a process for extracting useful substances from botanical matter.

FIG. 1 illustrates a process for extracting useful substances from botanical matter. The process may be implemented with a system that could include the apparatus illustrated schematically in FIG. 2, although this should not be considered a limitation. The illustrated apparatus includes a fresh solvent reservoir 200, a loaded solvent reservoir 202, a three-way diverter valve 204, a high pressure pump 206 and a hydraulic extraction device 208. The common port of the diverter valve 204 is connected to the high pressure pump 206 so that the valve can be used to connect either the fresh solvent reservoir 200 or the loaded solvent reservoir 202 to the intake port of the high pressure pump. The outlet port of the pump 206 provides pressurized solvent to an inlet of the hydraulic extraction device 208 via a high pressure line. The outlet of the hydraulic extraction device 208 is connected to the loaded solvent reservoir 202 via a low pressure line. In one implementation the high pressure pump 206 is a solvent reservoir with a top inlet connected to a compressed air tank and a bottom outlet capable of delivering solvent in a single pass through the hydraulic extraction unit. In one implementation the high pressure pump 206 is a manually operated syringe pump capable of delivering solvent in a single pass. In one implementation the high pressure pump 206 is a mechanically driven piston pump with inlet and outlet check valves capable of delivering solvent at 0-10 mL per minute at 4000 psi, such as a laboratory HPLC solvent delivery system. In one implementation the high pressure pump 206 is an air driven piston pump capable of delivering solvent at 1000 mL/minute at 5000 psi from 90 psi air, such as a series ASL-60-01 manufactured by Parker Hannifin Manufacturing Ltd.

Figure 2:
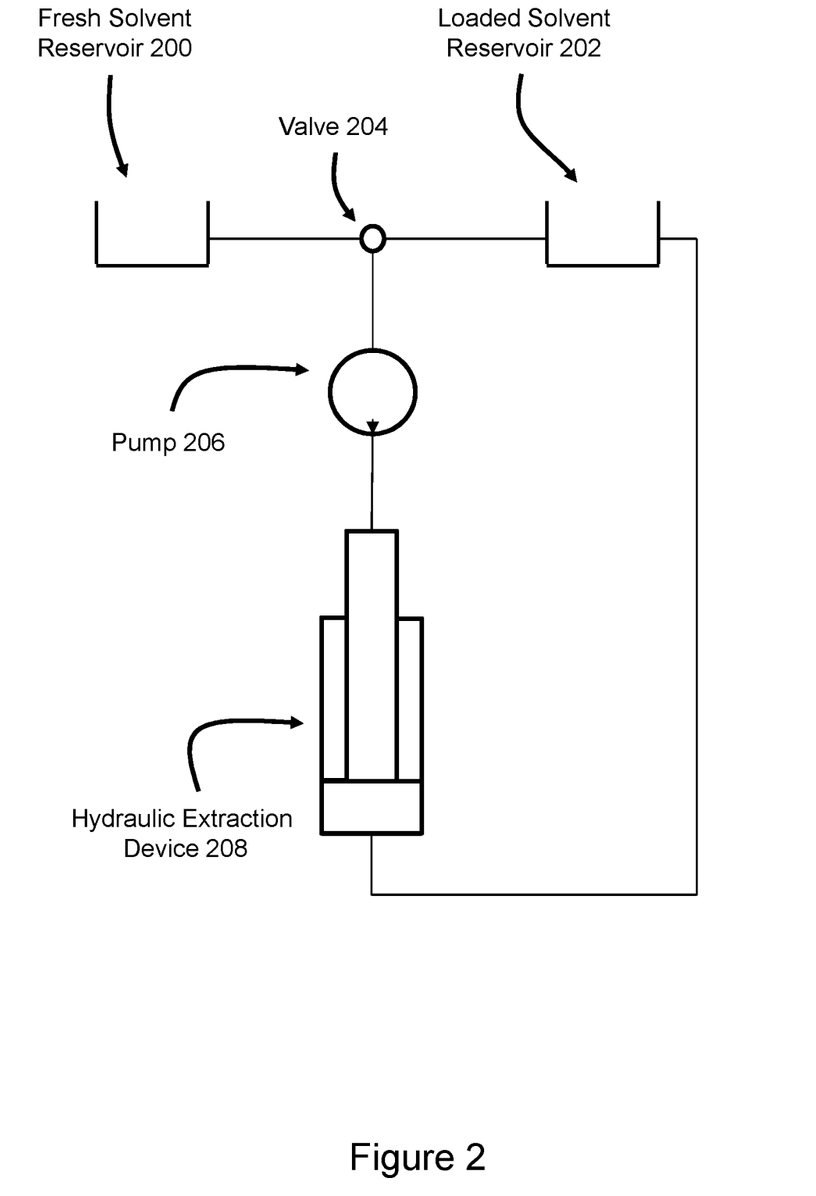
FIG. 2 is a schematic drawing of a system for extracting useful substances from botanical matter.

Referring to FIGS. 1 and 2, in step 100 the moisture content of the harvested botanical matter is reduced. The moisture content of freshly harvested green plant material may support undesirable microbiological growth. However, rapid drying such as with heat or vacuum may inhibit desirable maturation of the botanical matter. Moreover, freshly harvested botanical matter may include desirable "inactive" phytochemicals that could be lost as a result of drying or overly rapid drying. These phytochemicals may contribute to characteristics such as taste, aroma, and possibly bio-distribution and receptor binding of one or more active components. Consequently, partial drying, curing, protection from microbiological growth, and protection from loss of desirable volatile components are implementation details which may be determined based on the characteristics of the botanical matter being processed and desired results. For example, in order to mitigate loss of inactive phytochemicals a partial drying process may include implementation of a drying schedule characterized by periods during which moisture content is reduced at a controlled rate alternating with periods during which moisture content is held stable. In some implementations the harvested botanical matter is conventionally air dried to 8%-15% moisture by weight. In some implementations the plant matter may be partially dried, e.g., to reduce the moisture content to a range of 33%-50% moisture by weight, and then stored for some time in a sealed container, e.g., a couple of days, to effect a curing process. Subsequent to the curing step the partially dried plant matter may be further dried to reduce the final moisture content below that supporting microbiological growth.

Step 102 is to process the feedstock to reduce average particle size and fiber length. It should be understood that step 102 is not necessary in all implementations. For example, in some implementations whole plants or whole parts of plants are processed without reduction of average particle size and fiber length. Such processing of whole plants or whole parts may be advantageous because of reduced processing time, reduced energy input and reduced equipment requirements. Moreover, processing of whole plants or whole parts of plants may reduce dissociation of undesirable substance into the solvent and reduce losses of useful components to the milling equipment. However, in some instances it may be desirable to implement step 102, e.g. and without limitation when the useful substances would not otherwise be adequately exposed to solvent. Step 102 may be accomplished by rendering the feedstock into a smaller target range of particle size and fiber length, e.g. via a milling process. The harvested material may include particles and fibers in a wide range of sizes and lengths.

Average particle size and average fiber length can be reduced via the milling process, e.g., to 2.5-mm. Moreover, the distribution of particle sizes and fiber lengths can be controlled to within a predetermined range, e.g., to 0.5-10 mm. A wide variety of milling and other techniques might be employed. For example, and without limitation, milling may include the application of shearing force, compression force, or both. Some milling techniques require dried feedstock with moisture content below about 20% by weight, and typically between 8%-15%, where the plant material undergoes brittle fracture. Milling feed stock at a higher water content can be accomplished via a process that doesn't rely on brittle fracture to accomplish particle size reduction.

Step 104 is to mechanically compress the feedstock with the hydraulic extraction device 208. In some implementations the feedstock is subjected to mechanical compression force in the range of 500 to 10,000 psi (pound-force per square inch) by the hydraulic extraction device. Mechanical compression of the feedstock may result in a volumetric density of 20% w/v (weight/volume) to 80% w/v. The amount of compression force applied to the feedstock is an implementation detail that may be selected based on the type of botanical matter being processed, particle size, fiber length, solvent type, and process time. The feedstock is generally not compressed to a density so great that solvent is prevented from passing through the compressed feedstock, e.g. where fluidic paths through the feedstock are eliminated. However, under-compressed feedstock that allows solvent to pass through the compressed feedstock via low resistance pathways may result in uneven exposure of the feedstock to solvent and reduced dissolution efficiency, e.g. requiring more time and more solvent volume to extract a given amount of the useful substance from the feedstock. Compression settings for particular conditions may be determined heuristically.

Step 106 is to pump solvent through the compressed feedstock using the high pressure pump 206. Solvent is initially drawn from the fresh solvent reservoir 200 and pumped through the compressed feedstock while mechanical compressive force is applied to the feedstock by the hydraulic extraction device 208. For example, application of mechanical compressive force may be such that the volume of the compressed feedstock is maintained while the solvent traverses the feedstock, although transient volume changes may occur if the pump introduces solvent in high pressure pulses. A wide variety of solvents could be used, including but not limited to $CO_2$, butane, propane, alcohol, and various oils such as coconut oil, mineral oil, vegetable oil, grapeseed oil and flaxseed oil. Solvent is pumped through the compressed feedstock under pressure and collected in the loaded solvent reservoir 202. For example, the solvent may be pumped at a pressure in a range of 500 to 20,000 psi. Because application of mechanical compression force on the feedstock is maintained while the solvent is pumped through the feedstock, pressure in the range of 500 to 40,000 psi can be present at a surface where pressurized solvent is introduced to the feedstock in the hydraulic extraction device. Solvent pressure is ambient at a surface where the solvent exits the feedstock or the hydraulic extraction device unless the apparatus is operated in a closed loop configuration where the inlet pressure to the high pressure pump is either above or below ambient or there is a mechanical needle valve at the outlet channel to exert back pressure to the hydraulic extraction device. In all cases, there is a solvent pressure gradient presented across the feedstock between the inlet and the outlet. The mechanical compression applied to the feedstock helps to maintain the solvent pressure gradient, e.g., by limiting expansion of the volume of the feedstock and helps to minimize translocation of non-solubilized components due to the highly compacted nature of the compressed botanical feedstock. At least some of the useful substance (or substances) in the feedstock are dissociated from the feedstock and dissolved into the solvent as the solvent traverses the feedstock under pressure and thereby extracted from the feedstock. In some implementations the pumping of solvent is continuous, e.g. except for possible transient interruptions due to pump cycling and while solvent supply is selected by actuating the valve, the solvent is continuously pumped through the feedstock until processing is complete. The movement of solvent through the feedstock may enhance dissolution efficiency by increasing the volume of solvent in contact with the exposed surface area of the feedstock for a unit of time relative to static dissolution. Moreover, the flow of solvent under pressure and through highly compressed feedstock may present a steep shear gradient that helps to separate the useful substances from the feedstock. Partially loaded solvent is collected in the loaded solvent reservoir 202 via a low pressure flexible line when operated under ambient conditions at the outlet or via rigid return lines when operated under a closed loop configuration with either sub-ambient or high-pressure conditions at the outlet.

Step 108 is to recirculate partially loaded solvent through the compressed feedstock. As indicated above, at least some of the useful substance (or substances) in the feedstock are dissolved into the solvent as the solvent traverses the feedstock under pressure. Solvent that is partially loaded with useful substance is collected in the loaded solvent reservoir. When a sufficient volume has been collected in that reservoir the diverter valve 204 is actuated such that the pump 206 draws from the loaded solvent reservoir 202 rather than the fresh solvent reservoir 200. The partially loaded solvent is then recirculated through the compressed feedstock under pressure. Mechanical compression of the feedstock is maintained by the hydraulic extraction device 208 during pumping. Pumping partially loaded solvent through the compressed feedstock increases the concentration of useful substance in the solvent. The number of traversals of the feedstock by recirculated solvent and the concentration levels are implementation details. The result of step 108 is a loaded solvent that is captured in the loaded solvent reservoir 202. It should be understood that the loaded solvent is not necessarily saturated with useful substance.

In step 110 a volume of unloaded "fresh" solvent is pumped through the feedstock to effect a flush step. In order to do this the diverter valve 206 is actuated such that the pump 206 draws from the fresh solvent reservoir 200 rather than the loaded solvent reservoir 202. The unloaded solvent is pumped through the feedstock under pressure while mechanical pressure on the feedstock is maintained by the hydraulic extraction device 208. Partially loaded solvent exiting the feedstock may be collected and combined with the loaded solvent in the loaded solvent reservoir 202. The unloaded fresh solvent may be pumped through the feedstock until a predetermined level of substance concentration is achieved or until a predetermined volume of unloaded solvent has traversed the feedstock. Additionally, increasing the external compressive force while flushing reduces the bed volume thereby minimizing loaded solvent retention in the residue. While this step is not necessarily part of every implementation it can help to validate extraction efficiency.

In another implementation a single solvent reservoir is used. More particularly, a single reservoir is loaded with a volume of solvent which is pumped through compressed botanical matter under pressure as described above. However, the partially loaded solvent is fed back into the single reservoir. Partially loaded solvent from the reservoir may be pumped through the compressed botanical matter until extraction is complete or a desired level of concentration of the targeted substance in the solvent is achieved.

Figure 3:
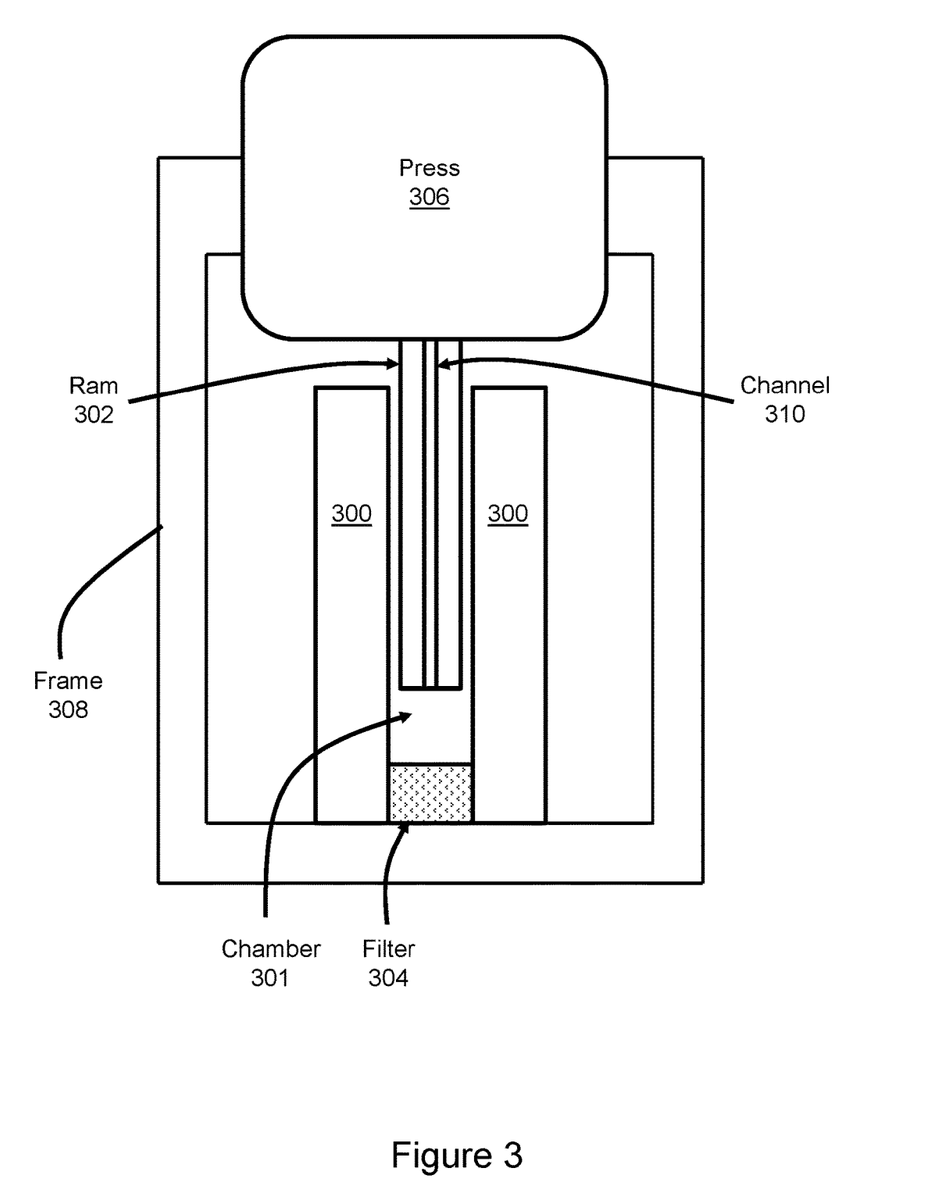
FIG. 3 illustrates an implementation of the hydraulic extraction device.

FIG. 3 illustrates an implementation of the hydraulic extraction device (208, FIG. 2). The hydraulic extraction device includes a chamber 301 having an interior volume defined by one or more walls 300, a ram 302, and a filter 304. The ram 302 is inserted into an open distal end of the chamber 301. The opposite distal end of the chamber is blocked by the filter 304. A press 306 applies force to the ram 302, thereby moving the ram within the chamber under control of an operator or computer. The press and chamber are maintained in a fixed positional relationship relative to one another by a rigid frame 308. Thus, movement of the ram 302 changes the interior volume of the chamber 302, i.e., the volume is decreased as the ram is inserted further into the chamber. Feedstock is inserted into the chamber for processing. The feedstock is mechanically compressed by application of force by the ram 302. The ram includes an internal channel 310 via which solvent can traverse the ram under pressure and be introduced to the compressed feedstock. The ram may be fitted with a nipple at a distal end of the channel opposite the frit in order to connect the tubing. The ram may transiently recoil in response to high pressure pulsing of the solvent. Filter 304 prevents the feedstock from exiting the chamber while permitting solvent to exit the chamber. Thus, solvent can flow through the compressed feedstock. The maximum particle size that can traverse the filter is an implementation detail, but a 20-60 micron filter could be used in one implementation. As will be described below, the hydraulic extraction device may be implemented with multiple parts that can be assembled and disassembled as part of the processing of botanical matter, e.g. to facilitate loading and unloading of feedstock.

Figure 4:
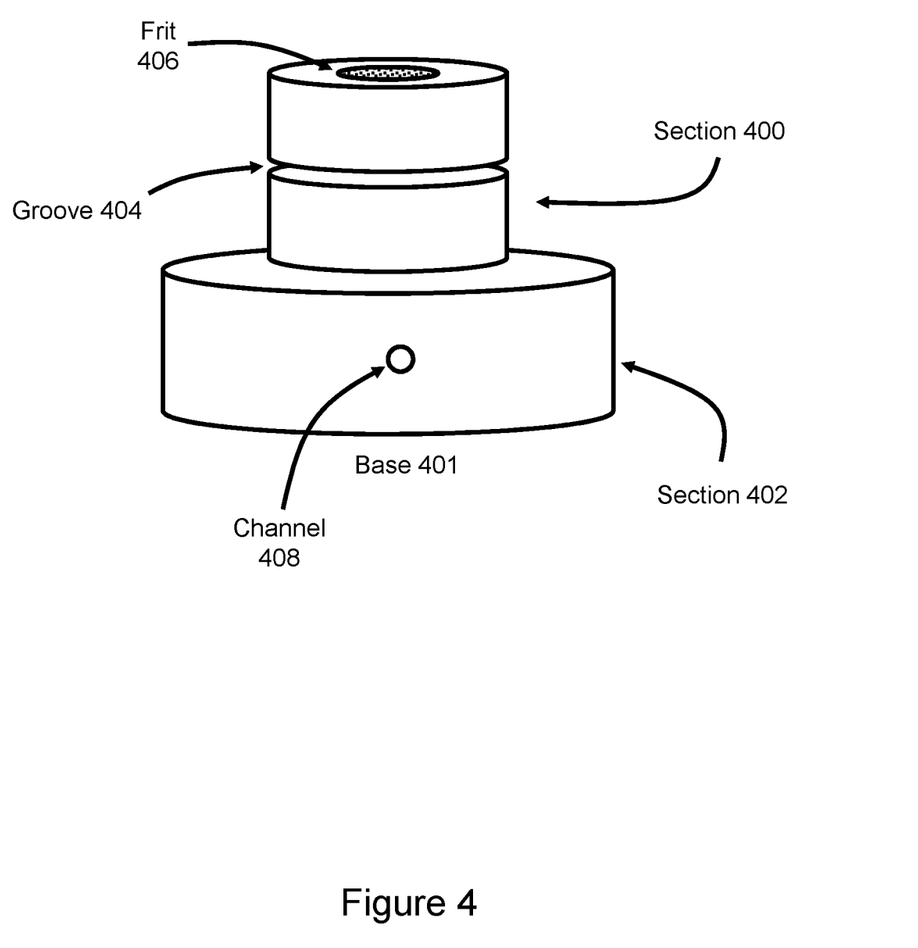
FIG. 4 illustrates a base section of a multi-part hydraulic extraction device.

FIG. 4 illustrates a base section 401 of a multi-part hydraulic extraction device. The base includes a relatively smaller cylindrical section 400 and a relatively larger cylindrical section 402. Both sections may be cast or machined from a single piece of material. The smaller section 400 includes a circular groove 404 in which an O-ring gasket (not specifically illustrated) is seated. A porous frit or rigid filter surface 406 which may be formed of sintered metal is disposed in the interior of the base with an exposed surface at a distal end of the smaller cylindrical section 400. A channel 408 formed in the larger section 402 traverses through to the frit 406 and allows fluid to flow from a distal end of the frit opposite to the exposed surface, through the base, and into external tubing. The base may be fitted with a nipple at a distal end of the channel opposite the frit in order to connect the tubing.

Figure 5:
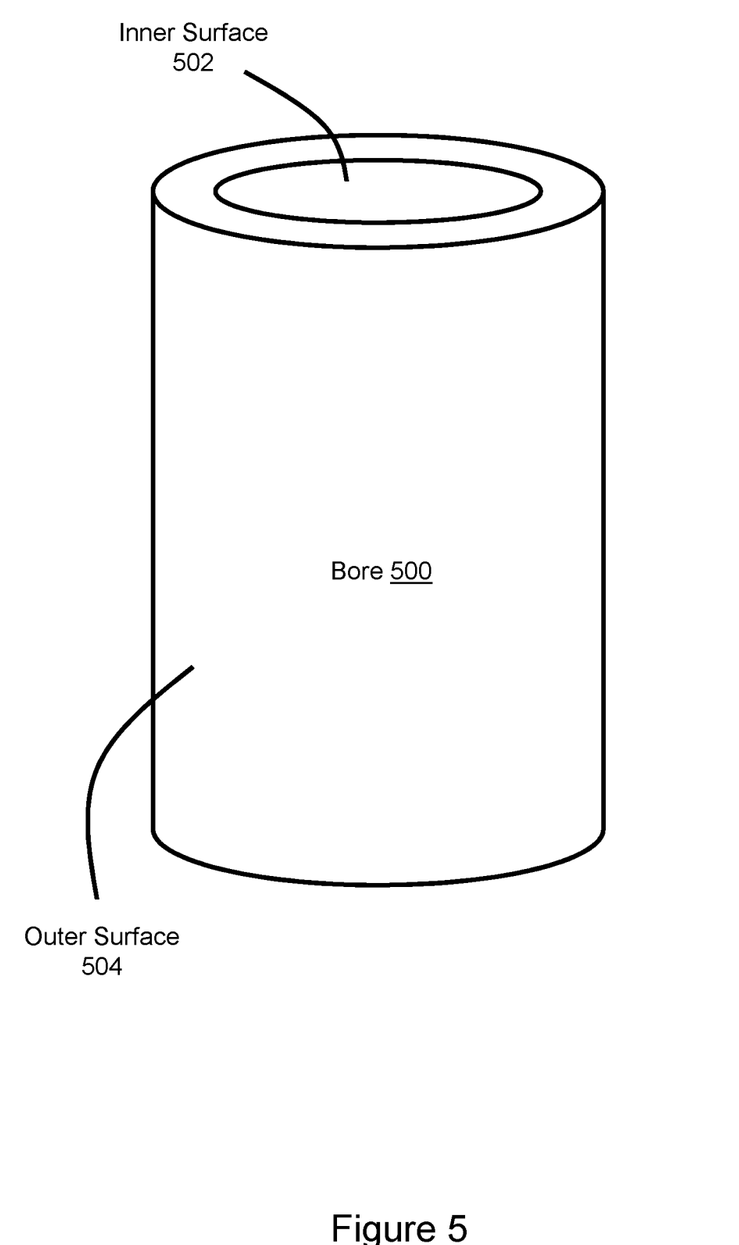
FIG. 5 illustrates a bore section of the multi-part hydraulic extraction device.

FIG. 5 illustrates a bore section 500 of the multi-part hydraulic extraction device. The bore is a cylinder with a wall having an inner surface 502, an outer surface 504 and distal ends. A diameter defined by the inner surface 502 accommodates the diameter of the smaller section (400, FIG. 4) of the base. In other words, the smaller section of the base can be inserted into a distal end of the bore until that distal end of the bore is seated against the larger section (402, FIG. 4) of the base. The gasket on the smaller section of the base mates against the inner surface 502 and prevents pressurized solvent from flowing between mated surfaces of the base and bore section. The bore wall thickness may be selected based in part upon the pressures it must withstand. Additionally, the wall thickness requirement depends upon the inside diameter of the bore. A larger inside diameter increases the load capacity of the bore and stress on the wall. Load capacity also increases with bore length. Wall stress doesn't increase with bore length, but load resistance at a given density does increase with length. Thus, to achieve a given flow rate a higher pressure may be required with a longer bore at a given packing density.

Figure 6:
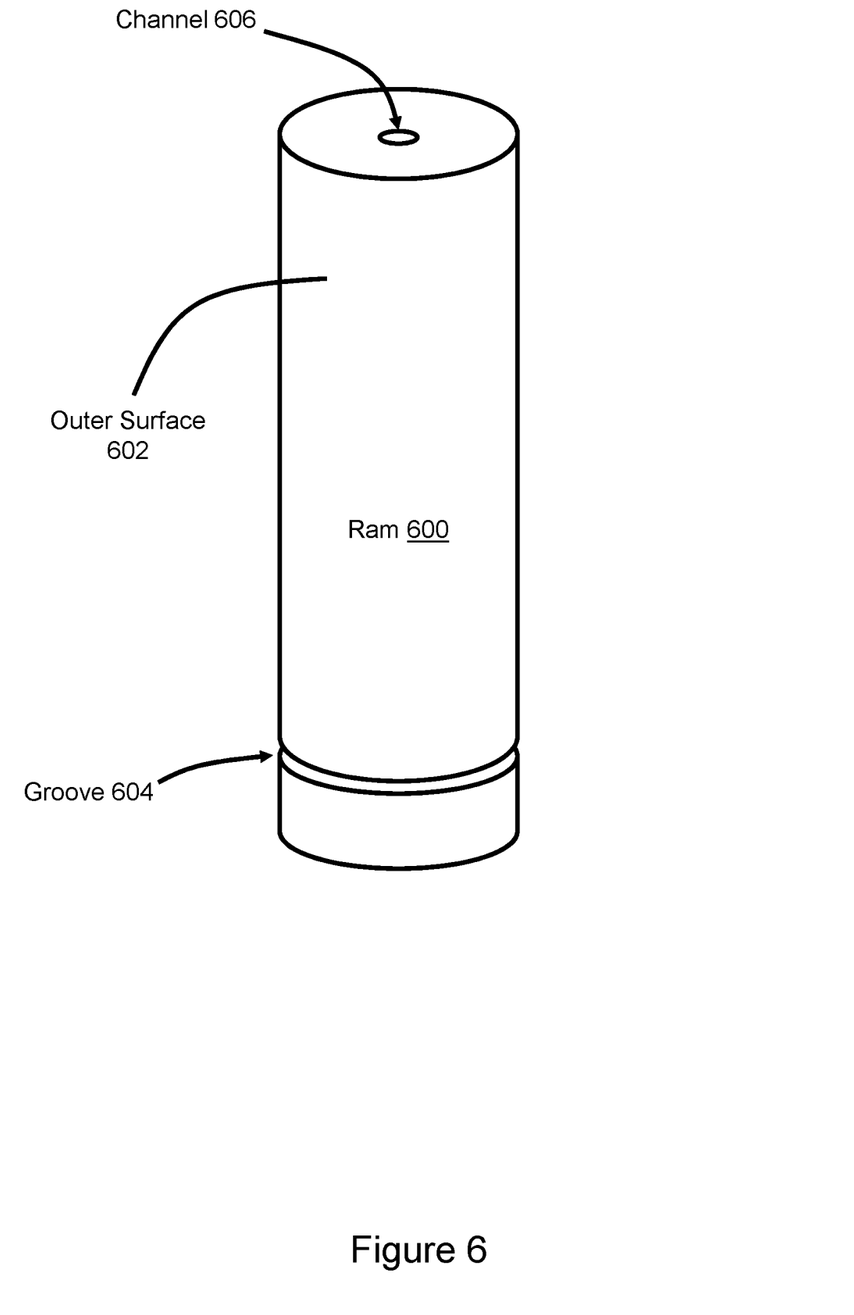
FIG. 6 illustrates a ram section of the multi-part hydraulic extraction device.

FIG. 6 illustrates a ram section 600 of the multi-part hydraulic extraction device. The ram is a cylinder with an outer surface 602 that defines an outer diameter corresponding to an inner diameter defined by the inner surface (502, FIG. 5) of the bore section. In other words, the ram section can be inserted into the bore section. A circular groove 604 formed in the outer surface 602 enables seating of a gasket. The gasket prevents pressurized solvent from flowing between the mated outer surface 602 of the ram section and inner surface (502, FIG. 5) the bore section. A channel 606 is formed through the ram section between distal ends. In other words, the channel traverses the ram from end to end.

Figure 7:
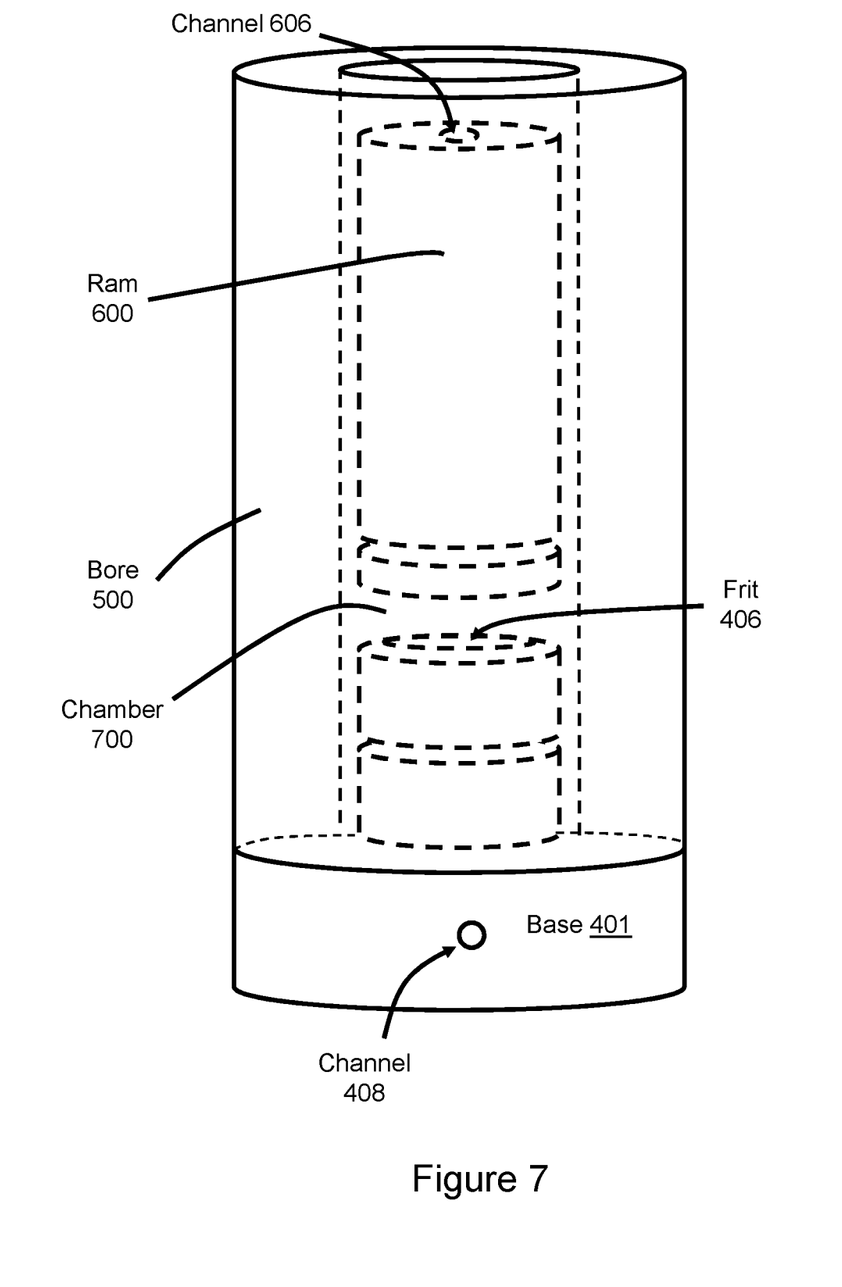
FIG. 7 illustrates the assembled multi-part hydraulic extraction device.

FIG. 7 illustrates the assembled multi-part hydraulic extraction device. The device may be partially assembled in preparation for processing botanical matter. More particularly, the bore section 500 is mounted on the base section 401. Botanical matter is then loaded into the resulting chamber 700. The loaded botanical matter is then compressed by inserting the ram 600 into the bore section 500 and applying compressive force against the botanical matter. While that compressive force against the botanical matter is maintained by the ram 600, solvent is pumped through the channel 606 in the ram under high pressure. The solvent is introduced to the botanical matter at the opposite distal end of the ram within the bore. The solvent traverses through the botanical matter and exits the hydraulic extraction device via the frit 406 and channel 408 in the base. As already explained above, the gasket between the base and bore, and also the gasket between the ram and bore, prevent pressurized solvent from leaking out of the extraction device. Alternatively, the solvent path can be reversed by connecting the base to the high pressure pump and the ram to the solvent collection vessel.

It should be understood that process factors including but not limited to feedstock type, feedstock particle size, solvent type, solvent viscosity, solvent pressure and feedstock mechanical compression pressure may affect process efficiency and product quality. For example, if the particle size of available feedstock decreases then efficiency and quality may be maintained by a commensurate reduction of feedstock compression. In general, one or more of high solvent pressure and feedstock mechanical compression may be dominant factors for maintenance of efficiency and quality. For example, it has been determined through experimentation that the process described above can reduce processing time by more than an order of magnitude while producing a product that has fewer undesirable substances in comparison with low pressure and ambient pressure solvent processes operating on lightly packed botanical matter. Thus some implementations of the inventive technique may provide improved extraction and purification, although this should not be interpreted as limiting. Improved purification and use of food-grade edible solvents may, in some implementations, enable production of a loaded solvent product that is ready for use in preparation of medicines or edible foodstuff. Such a product produced by the described process would represent an improvement over a product that includes inedible solvents or which requires cooling or other processing to remove impurities.

A number of implementations have been described. Nevertheless, it will be understood that additional modifications may be made without departing from the scope of the inventive concepts described herein, and, accordingly, other implementations are within the scope of the following claims.

What is claimed is:

1. A method comprising:
   mechanically compressing a botanical feedstock into compressed botanical feedstock by application of a compressive force of 500 to 10,000 pound-force per square inch;
   after compressing the botanical feedstock into compressed botanical feedstock, pumping a solvent through the compressed botanical feedstock at a pressure in a range of 500 to 20,000 pound-force per square inch, an amount of at least one substance present in the compressed botanical feedstock dissolving into the solvent to produce partially loaded solvent; and
   recovering the partially loaded solvent.

2. The method of claim 1 comprising reducing moisture content of the botanical feedstock prior to mechanically compressing the botanical feedstock.

3. The method of claim 1 comprising reducing average particle size and fiber length of the botanical feedstock prior to mechanically compressing the botanical feedstock.

4. The method of claim 1 comprising recirculating the partially loaded solvent by pumping the partially loaded solvent through the compressed botanical feedstock while applying compressive mechanical force against the compressed botanical feedstock to produce partially loaded solvent having a greater concentration of dissolved substance.

5. The method of claim 4 comprising pumping unloaded solvent through the compressed botanical feedstock while applying compressive mechanical force against the compressed botanical feedstock after recirculating the partially loaded solvent.

6. The method of claim 5 comprising repeatedly recirculating the partially loaded solvent.

7. The method of claim 1 comprising applying compressive mechanical force in a range of 500 to 10,000 pound-force per square inch against the compressed botanical feedstock while pumping the solvent through the compressed botanical feedstock.

* * * * *